US012167507B2

(12) United States Patent
Liu

(10) Patent No.: US 12,167,507 B2
(45) Date of Patent: Dec. 10, 2024

(54) ELECTRONIC VAPING DEVICE AND VAPOR GENERATING APPARATUS

(71) Applicant: Altria Client Services LLC, Richmond, VA (US)

(72) Inventor: Loi Ying Liu, Hong Kong (CN)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

(21) Appl. No.: 18/310,255

(22) Filed: May 1, 2023

(65) Prior Publication Data

US 2023/0269831 A1 Aug. 24, 2023

Related U.S. Application Data

(60) Continuation of application No. 16/882,946, filed on May 26, 2020, now Pat. No. 11,678,407, which is a
(Continued)

(30) Foreign Application Priority Data

Jul. 30, 2013 (HK) .................................. 131089169

(51) Int. Cl.
*H05B 1/02* (2006.01)
*A24F 40/10* (2020.01)
(Continued)

(52) U.S. Cl.
CPC .......... *H05B 1/0244* (2013.01); *A24F 40/42* (2020.01); *A24F 40/44* (2020.01); *A24F 40/50* (2020.01);
(Continued)

(58) Field of Classification Search
CPC .... A24F 47/008; H05B 1/0208; H05B 1/0244
(Continued)

(56) References Cited

U.S. PATENT DOCUMENTS 4,966,171 A * 10/1990 Serrano .................... A24D 1/22
131/194
9,204,670 B2 * 12/2015 Liu .......................... A24F 40/46
(Continued)

FOREIGN PATENT DOCUMENTS

CN 1205849 A 1/1999
CN 201379072 Y 1/2010
(Continued)

OTHER PUBLICATIONS

Extended European Search Report for Application No. 23163833.9, dated Jun. 30, 2023.
(Continued)

*Primary Examiner* — Nathaniel E Wiehe
*Assistant Examiner* — Thomas J Ward
(74) *Attorney, Agent, or Firm* — Harness, Dickey & Pierce, P.L.C.

(57) ABSTRACT

A flavored vapor generator (100, 200, 300, 400) used for an electronic smoking apparatus (10) comprises a housing; a liquid retention material (155, 255) which is filled, soaked or immersed with a flavored liquid and received inside the housing; an electric heater (150, 350, 450) for heating the liquid retention material (155, 255) to generate flavored vapor; and a sensor (156, 356, 456) for monitoring soaking or wetness conditions of the liquid retention material (155, 255) and providing signals for determining whether the flavored liquid in the liquid retention material (155, 255) is exhausted or almost exhausted.

18 Claims, 3 Drawing Sheets

Related U.S. Application Data division of application No. 14/907,837, filed as application No. PCT/IB2014/063541 on Jul. 30, 2014, now Pat. No. 10,694,782.

(51) Int. Cl.

| | | |
|---|---|---|
| A24F 40/42 | (2020.01) | |
| A24F 40/44 | (2020.01) | |
| A24F 40/50 | (2020.01) | |
| A24F 40/51 | (2020.01) | |
| A24F 40/53 | (2020.01) | |
| A61M 11/00 | (2006.01) | |
| A61M 11/04 | (2006.01) | |
| A61M 15/00 | (2006.01) | |
| A61M 15/06 | (2006.01) | |
| H05B 3/00 | (2006.01) | |

(52) U.S. Cl.
CPC .............. *A24F 40/51* (2020.01); *A24F 40/53* (2020.01); *A61M 11/005* (2013.01); *A61M 11/044* (2014.02); *A61M 15/001* (2014.02); *A61M 15/0085* (2013.01); *A61M 15/06* (2013.01); *H05B 1/0208* (2013.01); *H05B 3/0014* (2013.01); *A24F 40/10* (2020.01); *A61M 2205/583* (2013.01); *A61M 2205/8206* (2013.01)

(58) Field of Classification Search
USPC .......... 392/395; 131/329, 347; 219/201, 525
See application file for complete search history.

(56) References Cited

U.S. PATENT DOCUMENTS

| | | | |
|---|---|---|---|
| 2011/0265806 A1* | 11/2011 | Alarcon | A24F 40/485 |
| | | | 131/273 |
| 2011/0277764 A1 | 11/2011 | Terry et al. | |
| 2011/0278189 A1 | 11/2011 | Terry et al. | |
| 2012/0227752 A1 | 9/2012 | Alelov | |
| 2013/0056013 A1 | 3/2013 | Terry et al. | |
| 2013/0056014 A1 | 3/2013 | Noguchi et al. | |
| 2013/0192617 A1* | 8/2013 | Thompson | A24F 40/44 |
| | | | 131/329 |
| 2013/0263869 A1 | 10/2013 | Zhu | |
| 2013/0319435 A1 | 12/2013 | Flick | |
| 2014/0020693 A1 | 1/2014 | Cochand et al. | |
| 2014/0205272 A1* | 7/2014 | Midgette | A61L 9/037 |
| | | | 392/395 |

FOREIGN PATENT DOCUMENTS

| | | |
|---|---|---|
| CN | 201789924 U | 4/2011 |
| CN | 102106611 A | 6/2011 |
| CN | 201986689 U | 9/2011 |
| CN | 202014572 U | 10/2011 |
| CN | 202525085 U | 11/2012 |
| CN | 102894485 A | 1/2013 |
| CN | 202932039 U | 5/2013 |
| CN | 202932040 U | 5/2013 |
| CN | 103338664 | 10/2013 |
| CN | 103338665 | 10/2013 |
| CN | 105451582 A | 3/2016 |
| DE | 112011105101 | 1/2014 |
| EP | 2468116 A1 | 6/2012 |
| EP | 2468117 A1 | 6/2012 |
| EP | 2468118 | 6/2012 |
| EP | 2609820 A1 | 7/2013 |
| EP | 3027072 A1 | 6/2016 |
| EP | 3620069 A1 | 3/2020 |
| EP | 3925464 A1 | 12/2021 |
| JP | H11-033097 A | 2/1999 |
| JP | 2003-007514 A | 1/2003 |
| JP | 2012-223190 | 11/2012 |
| JP | 2014-501105 | 1/2014 |
| JP | 2014-501106 | 1/2014 |
| JP | 2014-501107 | 1/2014 |
| JP | 2016-525367 A | 8/2016 |
| KR | 20120051570 | 5/2012 |
| KR | 10-2013-0130759 | 12/2013 |
| KR | 10-2014-0004656 | 1/2014 |
| WO | WO-2011/124033 A1 | 10/2011 |
| WO | WO-2011/146315 A2 | 11/2011 |
| WO | WO-2011146174 A2 | 11/2011 |
| WO | WO-2012085203 | 6/2012 |
| WO | WO-2012085207 | 6/2012 |
| WO | WO-2012/129787 A1 | 10/2012 |
| WO | WO-2013/025585 | 2/2013 |
| WO | WO-2013020220 A1 | 2/2013 |
| WO | WO-2015/015431 A1 | 2/2015 |

OTHER PUBLICATIONS

Taiwanese Office Action for Application No. 111118330, dated May 26, 2023, and English translation thereof.
Supplemental Partial European Search Report issued Mar. 6, 2017, in European Application No. 14 83 1487.
Chinese Office Action issued Jun. 20, 2017 in Chinese Application No. 201480042294.2.
European Extended Search Report issued Jun. 16, 2017 in European Application No. 14831487.5.
Taiwanese Office Action issued Sep. 21, 2017 for Taiwanese Application No. 103126090.
Second Office Action issued Feb. 24, 2018 in Chinese Patent Application No. 201480042294.2.
Non-Final Office Action issued May 11, 2018 in Japanese Application No. 2016-530652.
European Patent Office Communication issued Jun. 29, 2018, in European Application No. 14 83 1487.
International Preliminary Report on Patentability issued Feb. 2, 2016 in International Application No. PCT/IB2014/063541.
Search Report issued Jun. 12, 2017 in Chinese Patent Application No. 2014800422942.
Written Opinion of the International Searching Authority for PCT/IB2014/063541 dated Jan. 12, 2015.
International Search Report issued Jan. 12, 2015 for PCT/IB2014/063541.
Third Office Action issued Sep. 20, 2018 in Chinese Application No. 201480042294.2.
Search report issued Apr. 18, 2018 in Japanese Application No. 2016-530652.
Taiwanese Office Action issued Feb. 27, 2019 in Taiwanese Patent Application No. 107122812.
Non-Final Office Action issued Aug. 13, 2018 in U.S. Appl. No. 14/907,837.
Final Office Action issued Feb. 14, 2019 in U.S. Appl. No. 14/907,837.
Non-Final Office Action issued Jul. 26, 2019 in U.S. Appl. No. 14/907,837.
Taiwanese Office Action issued Jul. 29, 2019 in Taiwanese Patent Application No. 107122812.
Taiwanese Office Action issued Nov. 28, 2019 in Taiwanese Patent Application No. 107122812.
Office Action issued on Feb. 7, 2020 in Japanese Application No. 2018-236177.
Extended European Search Report issued on Jan. 31, 2020 in European Application No. 19191668.3.
Notice of Allowance issued Feb. 24, 2020 in U.S. Appl. No. 14/907,837.
Notification of Reasons for Rejection issued Jun. 25, 2021 in Japanese Application No. 2020-139103.
Extended European Search Report dated Nov. 16, 2021.
Japanese Office Action and English translation thereof dated Dec. 24, 2021.
Taiwanese Office Action and English translation thereof dated Jan. 22, 2022.

(56) References Cited

OTHER PUBLICATIONS

Taiwanese Office Action and English translation thereof dated Jun. 28, 2022.
Taiwanese Office Action for corresponding Application No. 110102327, dated Nov. 11, 2022. and English translation thereof.
Japanese Office Action for Application No. 2023-075429, dated Jun. 21, 2024, with English translation.

* cited by examiner

ELECTRONIC VAPING DEVICE AND VAPOR GENERATING APPARATUS

CROSS-REFERENCE TO RELATED APPLICATIONS

This application is a Continuation of U.S. application Ser. No. 16/882,946, filed on May 26, 2020, which is a Divisional of U.S. application Ser. No. 14/907,837, filed on Jan. 27, 2016, which is the U.S. National Phase of International Application No. PCT/IB2014/063541, filed on Jul. 30, 2014, which claims priority to Hong Kong Application No. 13108916.9, filed on Jul. 30, 2013, the entire contents of each of which are incorporated herein by reference.

The present disclosure relates to flavoured vapour generating apparatus and electronic smoking apparatus, and more particularly to flavoured vapour generators of electronic smoking apparatus.

BACKGROUND

Electronic smoking apparatus such as electronic cigarettes are gaining increasing popularity and acceptance as a replacement of conventional paper based cigarettes.

An electronic cigarette typically includes a flavoured smoke generator and electronic circuitry which are housed in an elongate housing. The elongate housing is adapted for finger holding and comprises a mouth piece which defines an air passage way connecting the flavoured smoke generator to a user such that smoke flavoured vapour generated in response to a suction action by a user will be delivered to the user via the mouth piece.

The electronic circuitry typically comprises an electric heater which is to operate to heat up a medium which is soaked with a flavoured liquid. The medium is usually a liquid affinity medium or a liquid retention medium such as cotton or glass fibre. The flavoured liquid, also known as e-juice or e-liquid, is usually a solution comprising organic substances, such as propylene glycol (PG), vegetable glycerine (VG), polyethylene glycol 400 (PEG400) mixed with concentrated flavours, liquid nicotine concentrate, or a mixture thereof.

A flavoured smoke generator typically comprises a cartridge and an atomiser. A cartridge is usually a small plastic, glass or metal container with openings at each end which is adapted to serves as both a liquid reservoir holding the flavoured liquid and a mouthpiece. An atomizer is provided to cause vaporization of the flavoured liquid and typically contains a small heater filament and a wicking material which draws the flavoured liquid from the reservoir of the cartridge in contact or in close proximity to the heater filament. When the electronic cigarette operates, the heater filament will heat up the liquid soaked wicking material and flavoured smoke will be generated for delivery to a user.

When a cartridge and an atomizer are integrated, the resulting device is known as a cartomizer.

While there is no actual burning of paper or tobacco during operation of an electronic cigarette, overheating of a flavoured smoke generator may occur when there is no or insufficient flavoured liquid. Such overheating is adverse and may pose health consequences or complications which are yet unknown or unclear.

DESCRIPTION OF FIGURES

The disclosure will be described by way of non-limiting example with reference to the accompanying Figures, in which:—

DESCRIPTION

Figure 1:
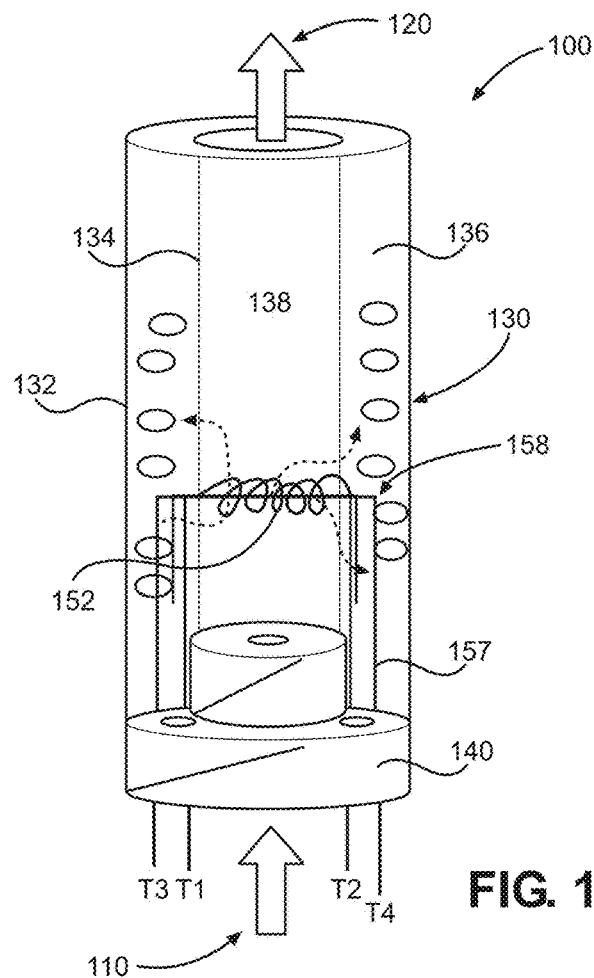
FIG. 1 is a schematic diagram of an example flavoured vapour generator according to the present disclosure.

A flavoured vapour generator 100 depicted in FIG. 1 comprises an air inlet at an air inlet end 110, a flavoured vapour outlet at a flavoured vapour outlet end 120, and a main body 130 interconnecting the air inlet end 110 and the flavoured vapour outlet end 120. The main body 130 is substantially cylindrical and includes a rigid housing which extends axially between the air inlet end 110 and the flavoured vapour outlet end 120. An electric heater comprising an electric wire 152, an exposed or naked liquid retention device 154 comprising a plurality of liquid retention wicks 155 and a wetness sensor 156 are supported on the main body. The main body is attached to a base 140 which defines the air inlet end. The rigid housing of the main body includes an outer peripheral wall 132 and an inner peripheral wall 134 which is surrounded by the outer peripheral wall 132. The space between the outer peripheral wall and the inner peripheral wall collectively define a first hollow compartment 136 which is adapted to hold a supply of flavoured liquid. This hollow compartment 136 defines a reservoir for storing a volume of flavoured liquid for dispensing to the exposed or naked liquid retention device.

The inner space which is surrounded by the inner peripheral wall 134 defines a second hollow compartment 138 inside the main body 130. This hollow compartment 138 defines a hollow passage channel through which flavoured vapour generated by operation of the heater will travel out of the vapour generator 100. The inner and outer peripheral wall are substantially cylindrical and co-axial or concentric such that the first hollow compartment forms a substantially circular chamber which surrounds the second hollow compartment.

The exposed liquid retention device 154 extends between a first liquid outlet on a first sidewall of the reservoir 136 and a second liquid outlet on a second sidewall of the reservoir 136 which is oppositely facing the first liquid outlet. The liquid retention device 154 comprises a plurality of wicks which projects across the second hollow compartment 138. The wicks are formed form a bundle of fibrous liquid retention materials 155 such as fibre glass threads and flavoured liquid stored in the reservoir will be guided to move from the first and/or second liquid outlets along the wicks to get exposed in the second hollow compartment 138.

The example flavoured vapour generator 100 is a cartomiser that is packaged in the form of a disposal cartridge. The cartridge is adapted for attaching to a main body of an electronic cigarette to facilitate simulated smoking operation. The air inlet end is for coupling to the main body of an electronic cigarette and the base portion includes a 'snap on' or threaded end portion for fastening to the main body of an electronic cigarette. The portion of the cartridge proximal the flavoured vapour outlet end 120 is adapted to a mouth piece adapted for oral contact by a user.

Figure 2:
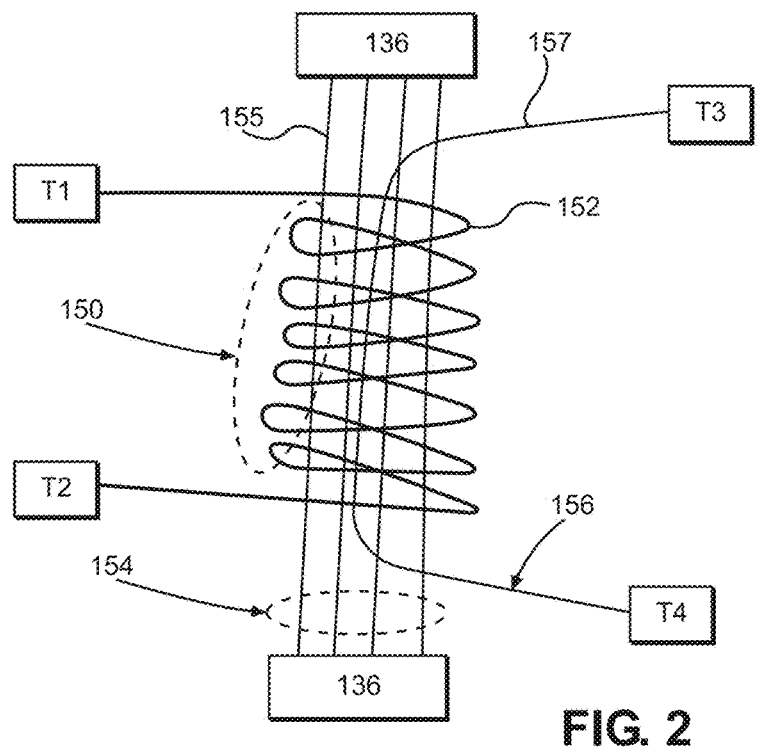
FIG. 2 is a schematic diagram depicting an assembly of a liquid retention material and an electric heater of the flavoured vapour generator of FIG. 1.

The electric heater is coupled to the portions of the wicks which are exposed inside and across the second hollow compartment 138. As depicted in FIG. 2, the electric heater includes a heating wire 152 which is wound into a plurality of windings. The plurality of windings formed by the heater wire is attached to a bundle of glass fibres 155 which collectively define an example naked liquid retention device 154. The example liquid retention wicks comprise a plurality of glass fibres which are twisted into a strand of glass fibres. The glass fibres are filled with the flavoured liquid through wicking of flavoured liquid from the reservoir 136. An assembly comprising the wound heating filament and the strand of glass fibres is supported on the main body and extends transversely across the second hollow compartment in a bridge-like manner. The assembly comprising the bundle of the glass fibres and the wound heating filament is elongate and extends in an axial direction. The axial ends of the assembly penetrates or projects into the second hollow compartment to tab into a reservoir of flavoured liquid formed inside the second hollow compartment to secure a continuous supply of the flavoured liquid for repeated operation.

The assembly comprising the wound heating filament and the strand of glass fibres is supported on the main body by a rigid wire frame which projects from the base 140. The rigid wire frame 158 is made of a rigid conductive wire such as a copper or nickel coated iron wire. The wire projects from the base and extends upwardly inside the first hollow compartment 136, bends orthogonally at an elevation level above the base to pass through the inner peripheral wall and enters the second hollow compartment 138, extends across the second hollow compartment at substantially the same elevation level, passes through the inner peripheral wall again and enters the first hollow compartment 136 again at a location which is approximately diametrically opposite to the location from which it exits from the first hollow compartment for the first time, and bends orthogonally downwards to the reach the base. The end portions of the resistive wire project through the base 140 portion to define contact terminals T3, T4 which are accessible from the side of the base 140 which is away from the second hollow compartment. The base may be made of an insulating material or the end portions of the resistive wire may insulated to avoid short-circuiting and to facilitate external terminal connection.

The assembly comprising the wound heating filament and the strand of glass fibres are arranged such that an exposed portion of the resistive wire is embedded inside the strand of fibres such that the exposed portion of the resistive wire is separated from the heater filament. In an example, the filament is wound around the strand of glass fibres into a plurality of windings and resistive wire is located at the axis of a coil formed by the filament winding. The approximately central location of the resistive wire inside the coil would promote a more even measurement of resistance inside the liquid retention material to mitigate local variation. As the portion of the heater filament is wound about the strand of glass fibres, and the stand of glass fibres is in turn held on the portion of the rigid wire extending across the second hollow compartment, the rigid frame of the rigid resistive wire provides a support to reinforce the strength and reliability of the heating filament. Contact terminals T1, T2 of the electric heater are also accessible from the same side of the base 140 on which the sensor terminals T3, T4 are present.

Flavoured liquid such as a solution comprising organic substances, such as propylene glycol (PG), vegetable glycerine (VG), polyethylene glycol 400 (PEG400) mixed with concentrated flavours, liquid nicotine concentrate, or a mixture thereof is stored inside the first hollow compartment. The flavoured liquid is stored inside the first hollow compartment by filling the first hollow compartment with liquid absorbents such as cotton or other fabric materials that are soaked with the flavoured liquid. Such an arrangement provides a continuous supply of flavoured liquid while mitigating sealing requirements. For example, such an arrangement will mitigate excessive leakage of the flavoured liquid at the junctions at which the assembly comprising the heating filament and the strand of glass fibres enters or leaves the first hollow compartment.

During normal use, operation of the electric heater will generate heat to cause vaporization of the flavoured liquid stored inside the assembly. After vaporization has taken place, capillary or similar effects will cause the strand of glass fibres to wick and replenish the flavoured liquid from the reservoir of flavoured liquid. The process will repeat until the flavoured liquid inside the reservoir is dried up. Further heating of the assembly under such circumstances when the reservoir has dried up may heat or overheat the assembly to a very high temperature. Such overheating is adverse and may bring about non-desirable side effects or complications which are not yet known.

To mitigate such adverse circumstances, the wetness or soaking conditions of the strand of glass fibres is monitored. In devising schemes to determine the wetness or soaking conditions of the strand of glass fibres in order to utilize the information to determine whether the reservoir or the strand has dried up, it is noted that although the types of flavoured liquid commonly used for simulating smoking by electric heating is oily or oil based, some degree of electrical conductivity is detectable. In the present example, the wetness or soaking conditions are monitored by measuring resistance between the wound heater filament and the portion of the rigid resistive wire embedded inside the strand of glass fibres.

Example resistance measurements made on various combination of terminals between a contact terminal on the heater (one of T1 and T2) and a contact terminal on the sensor (one of T3 and T3) using a Fluke™ 189 meter are set out in table 1 below:

TABLE 1

| Measuring terminals | | resistance (MΩ) | |
|---|---|---|---|
| | | dry | wet |
| T1 | T3 | OL | 2.13 |
| T3 | T1 | OL | 2.25 |
| T1 | T4 | OL | 2.31 |
| T4 | T1 | OL | 2.12 |
| T2 | T3 | OL | 2.10 |
| T3 | T2 | OL | 2.21 |
| T2 | T4 | OL | 2.20 |
| T4 | T2 | OL | 2.16 |

In table 1 above, the symbol 'OL' means over limit and the specified limit was noted to be 40 MΩ. A wet condition means the strand of glass fibres is fully soaked with a flavoured liquid such as an e-juice or an e-liquid.

In light of the above, it is noted that the resistance between a sensor terminal and a heater terminal may be used as an indication that the strand of glass fibres is wet or is dried up. It will be appreciated that the term 'wet' or 'dried' in the present context is with reference to favoured liquids, especially flavoured liquids for generating simulated smoke effect by electric heating, and has no bearing to water wetness.

To utilize the phenomenon, a threshold value of resistance between a sensor terminal and a heater terminal may be selected as indicative of the wetness or dryness of the liquid retention material. For example, a measured resistance value of above 3 MΩ between a sensor terminal and a heater terminal may be selected as an threshold operational resistance below which the strand of glass fibre is sufficiently wet to be operational and above which the strand of glass fibres is dried up and is not suitable for operation.

Where a higher measurement margin is to be allowed, the threshold non-operation resistance that is indicative of non-operational dryness may be set to 4 MΩ, 5 MΩ, 10 MΩ, 20 MΩ, 30 MΩ, or even higher, as the resistance will increase rapidly when the strand of glass fibres becomes dry of e-juice.

On the other hand, the threshold operational resistance that is indicative of a wetness level suitable for operation may be set to be below 6 MΩ, 5 MΩ, 4 MΩ, 3 MΩ, or 2.5 MΩ without loss of generality.

Figure 3:
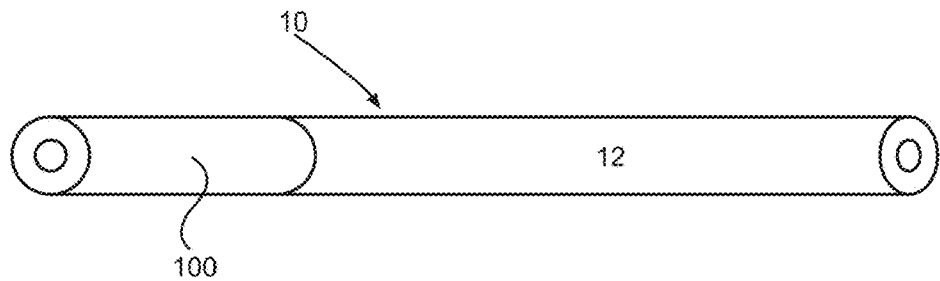
FIG. 3 depicts an electronic smoke incorporating a flavoured vapour generator of FIG. 1.

An example electronic cigarette 10 depicted in FIG. 3 comprises a first elongate body 12 and a cartomiser cartridge 100 of the present disclosure attached to an axial end of the first elongate body. The first elongate body and the rigid housing have the same outer shape and lateral dimensions such that the electronic cigarette appears as a single piece. The first elongate body defines an air inlet, an air outlet and a bore interconnecting the air inlet and the air outlet. The air outlet end of the first elongate body is for mechanical coupling with the air inlet end of the cartomiser and comprises a mechanical coupling means which is complementary to that on the air inlet end of the cartomiser. A control circuit 14 (e.g., an electronic controller), battery 16 and a visual indicator 18 such as an LED indicator are installed inside the elongate body. Contact terminals are disposed on the air outlet end of the first elongate body to facilitate contact of the heater terminals T1, T2 and sensor terminals T3, T4 with their counterpart inside the control circuitry. The control circuit includes an operation circuit to activate the electric heater and a decision circuit which is arranged to deactivate or limit the power supply to the electric heater upon detection that the wetness or soaking conditions at the strand of glass fibres are not suitable for heating operation. The control circuit may decide whether the wetness or soaking conditions are suitable for operation with reference to the resistance measured between a sensor terminal and a heater terminal as indicated above and without loss of generality.

Figure 5:
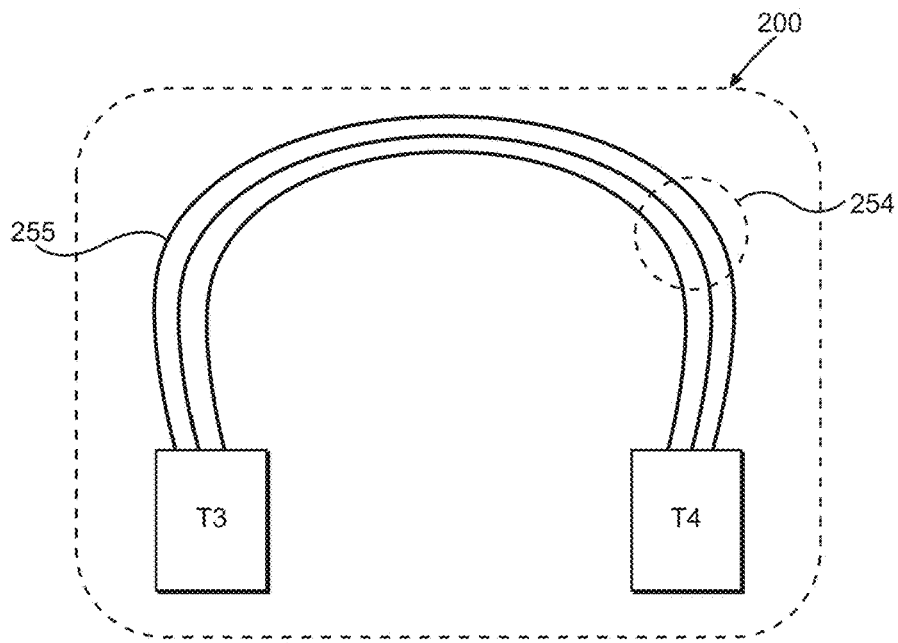
FIG. 5 is schematic diagram depicting features of an example flavoured vapour generator.

FIG. 5 shows another example flavoured vapour generator 200 according to the disclosure. This example flavoured vapour generator is a modification from the example flavoured vapour generator 100 but with the non-conductive or insulating wicks directly used as a sensing device. In this example, output terminals of the sensor 254 are connected to the lengthwise ends of the wicks 255. As the resistivity of the wicks will change substantially depending on whether or not the wicks are filled, and whether the wicks are fully or partially filled with the flavoured liquid, information on such resistance properties can be used to determine operation of the electronic cigarette. In this example, other features are the same as that of the flavoured vapour generator 100 and the description of those other features are incorporated by reference with feature numerals increased by 100.

Figure 6:
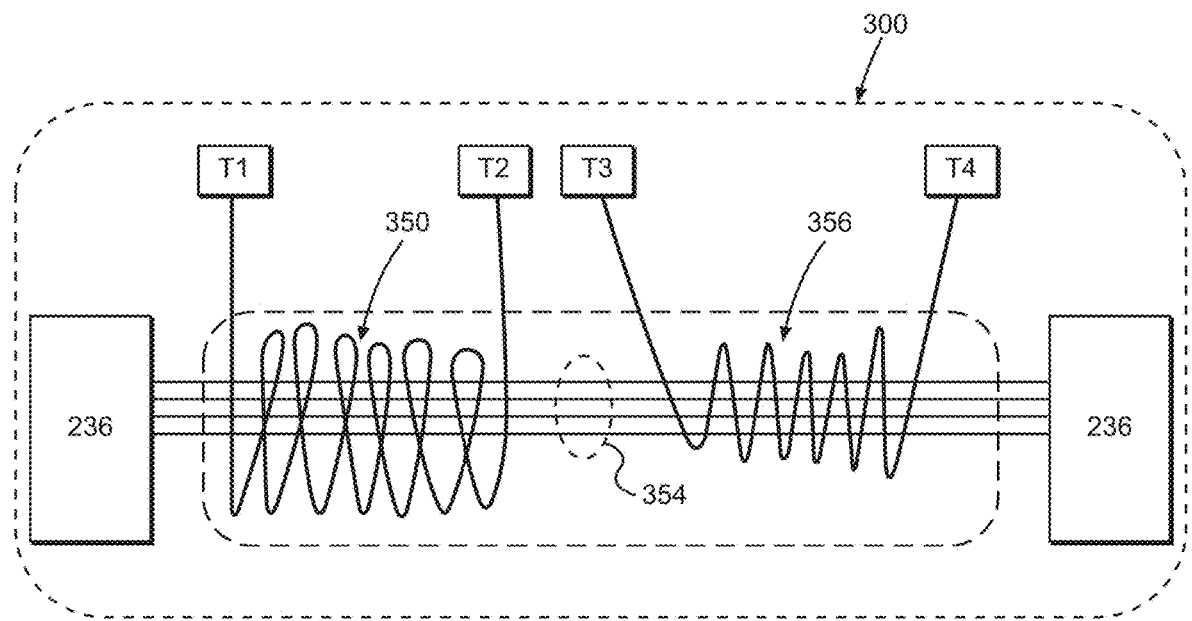
FIG. 6 is schematic diagram depicting features of an example flavoured vapour generator.

FIG. 6 shows another example flavoured vapour generator 300 according to the disclosure. This example flavoured vapour generator is a modification from the example flavoured vapour generator 100 but with the conductor forming the sensing device of the sensor operating as a second converter for converting the flavoured liquid into flavoured vapour. In this example, the conductor 356 forming the sensing device of the sensor is wound about the wicks and can operate as a parallel converter. In this example, other features are the same as that of the flavoured vapour generator 100 and the description of those other features are incorporated by reference with feature numerals increased by 200.

Figure 7:
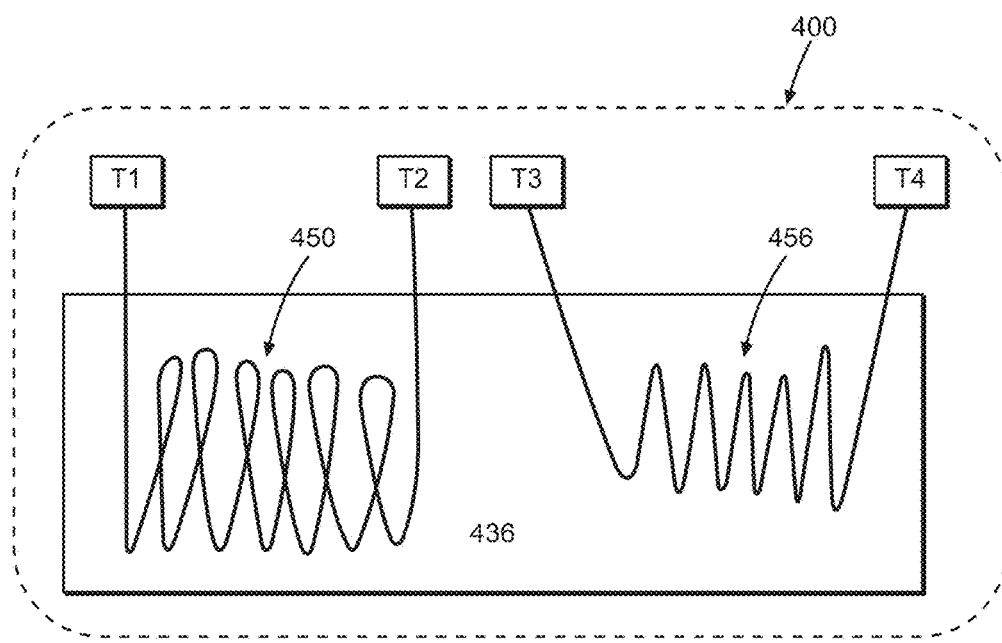
FIG. 7 is schematic diagram depicting features of an example flavoured vapour generator.

Another example flavoured vapour generator 400 depicted in FIG. 7 is a modification to that of the flavoured vapour generator 300. In this example, both the heater 450 and the sensor 456 are immersed inside a reservoir 436. As both the heater 450 and the sensor 456 are immersed inside a reservoir 436, no wick to draw flavoured liquid from the reservoir is required. During operation, flavoured liquid stored inside the reservoir will be heated to produce flavoured vapour and to travel to the flavoured vapour outlet via the hollow passage channel. Other features are the same as that of the flavoured vapour generator 300 and the description of those other features are incorporated by reference with feature numerals increased by 100. The sensor heater may be selectively activated to increase converter operation power where necessary.

The flavoured vapour generating apparatus disclosed herein comprises a liquid retention device which comprises fibrous liquid retention materials for retaining a flavoured liquid, a liquid reservoir to supply a flavoured liquid to the fibrous liquid retention materials of the liquid retention device, a converter which is operable by electrical power to convert flavoured liquid on the fibrous liquid retention materials into flavoured vapour, and a sensor. The sensor is arranged to provide information on the amount or density of flavoured liquid being retained on the fibrous liquid retention materials.

Figure 4:
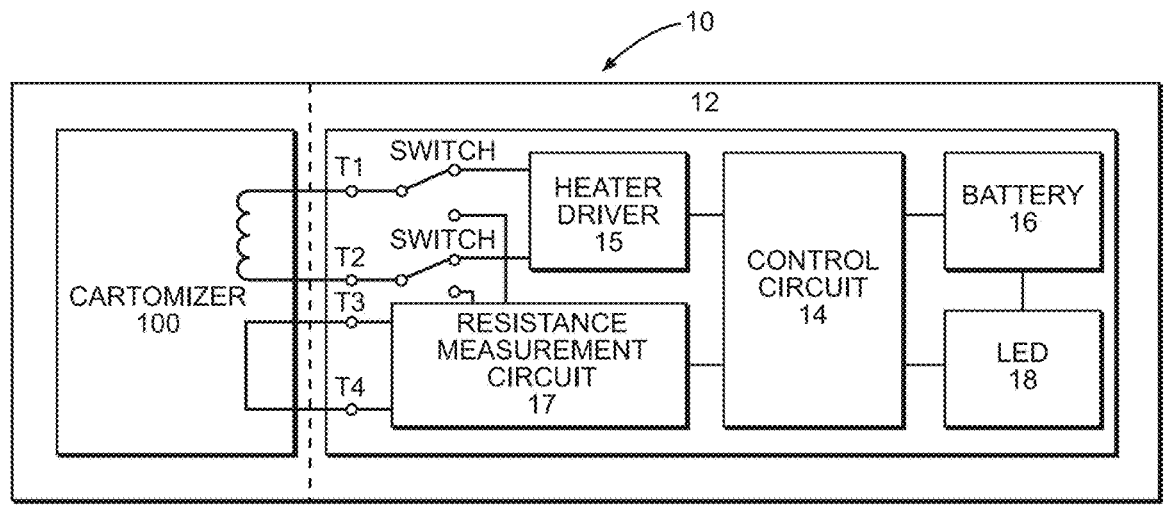
FIG. 4 is a functional block diagram of an electronic cigarette of FIG. 3.

In some embodiments, the liquid retention device and the liquid reservoir are merged or combined and no fibrous liquid retention material is required or necessary, and both the converter and the sensor are immersed in a liquid bath of flavoured liquid. In such embodiments, the flavoured vapour generating apparatus comprises a liquid retention device, which is also a liquid reservoir to store a flavoured liquid, a converter which is operable by electrical power to convert stored flavoured liquid into flavoured vapour, and a sensor; wherein the sensor and the converter are immersed in a liquid bath of the stored flavoured liquid. In such embodiments, the sensor and the converter are electrically connected thorough the liquid bath. Electrical properties such as resistance and capacitance between the converter and the sensor will change or vary according to the level of the liquid bath, or the extent of relative immersion of the converter and the sensor. By detecting the electrical properties which are due to separation of the converter and the sensor with the flavoured liquid as a connection medium, information on the wetness or whether the remaining level of the flavoured liquid has dropped to a threshold minimum can be obtained and utilised. Where capacitance is to be measured in combination with the measurement of resistance, the circuit part 17 of FIG. 4 will be modified respectively as a circuit for measuring resistance and capacitance or as a circuit for measuring capacitance without loss of generality. Furthermore, while circuit part 15 of FIG. 4 is marked as a heater driver, the circuit may be referred to as a "converter driver" where appropriate.

There is disclosed an electronic smoking apparatus comprising a flavoured vapour generating apparatus herein, wherein the electronic controller is to control operation of the converter to generate smoke flavoured vapour with reference to output of the sensor.

There is also disclosed a flavoured vapour generator for use with an electronic smoking apparatus. The flavoured vapour generator comprises a housing, a liquid retention material which is filled soaked or immersed with a flavoured liquid and received inside said housing, an electric heater to heat up the liquid retention material to generate flavoured vapour, and a sensor to monitor soaking or wetness conditions of the liquid retention material and to provide signals for facilitating determination of whether the soaking or wetness conditions of the liquid retention material corresponds to a condition of exhaustion or near exhaustion of said flavoured liquid in said liquid retention material.

There is further disclosed a flavoured liquid generator, wherein said housing defines a first hollow compartment inside which said flavoured liquid is stored and a second compartment defining an air inlet, a flavoured air outlet and an air passageway interconnecting the air inlet and the air outlet; wherein an assembly comprising said liquid retention material and said electric heater extends from said first hollow compartment into said air passageway such that air coming in from said air inlet due to suction at said air outlet will encounter said assembly before reaching said flavoured air outlet.

In some embodiments, the apparatus is a cartomizer which is detachably attachable to a main body of an electronic smoking apparatus, and the liquid contained inside the liquid reservoir is to facilitate the flavoured vapour generating apparatus to operate as a smoke flavoured source of an electronic smoking apparatus.

The sensor may be adapted to monitor soaking or wetness conditions of the liquid retention material and to provide signals for facilitating determination of whether the soaking or wetness conditions of the liquid retention material corresponds to a condition of exhaustion or near exhaustion of said flavoured liquid in said liquid retention material.

Inclusion of a wetness sensor in a flavoured vapour generator for use with an electronic smoking apparatus is advantageous since information on the wetness or dryness at the liquid retention material can be utilized to facilitate operation control of an electronic cigarette.

The fibrous liquid retention materials may be made of cotton, fibre glass or other fibrous materials that can wick and hold a flavoured liquid such as liquids known as e-juice or e-liquid, whether nicotine containing or not.

The fibrous liquid retention materials may be formed as threads, yarns or strings, whether twisted or not.

The flavoured liquid may be an oily substance and the sensor comprises a probe to detect electrical resistance conditions inside said liquid retention material. The flavoured liquid may be primarily organic based, such as glycol or glycerine based, and said sensor is to monitor electrical property such as conductivity or resistivity within or across said liquid retention material during operation to facilitate determination of wetness or dryness of said liquid retention material.

While oil-based flavoured liquids are generally known to be non-conductive, their small conductivity is nevertheless useful to provide simple fast and useful wetness measurements to facilitate electronic smoke operation control.

The electric heater may comprise a heating element which is attached to said liquid retention material and maintained in contact therewith to facilitate contact heating to generate said flavoured vapour, and said sensor comprises a probe wire portion embedded inside said liquid retention material.

The heating element may comprise a heating filament which is wound on said liquid retention material to form a plurality of windings and said probe wire portion is surrounded by and spaced apart from said windings.

The liquid retention material may comprise a bundle of liquid absorbing fibres or fibre strands which collectively extends in a first direction to define a wicking direction, and said heating element is wound around said first direction to define a winding core containing said liquid retention material.

The said housing may be metallic and define a first hollow compartment inside which said flavoured liquid is stored and a second compartment defining an air inlet, a flavoured air outlet and an air passageway interconnecting the air inlet and the air outlet; wherein an assembly comprising said liquid retention material and said electric heater extends from said first hollow compartment into said air passageway such that air coming in from said air inlet due to suction at said air outlet will encounter said assembly before reaching said flavoured air outlet.

In some embodiments, the second hollow compartment is surrounded by said first hollow compartment, and two ends of said assembly projects into said first hollow compartment to wick said flavoured liquid into said liquid retention material.

The assembly may form a bridge which is suspended on opposite sides of the first hollow compartment and extends across said second hollow compartment.

The flavoured liquid may be stored in said second hollow compartment and is resident on a liquid absorbent substance such as cotton for wicking delivery to said liquid retention material inside said second hollow compartment.

The assembly of said liquid retention material and said heater may extend in a direction which is substantially transverse to direction of air flow from said air inlet to said flavoured vapour outlet during normal operation.

The generator may be arranged such that an electrical resistance between said sensor and said electric heater that is below a threshold operation resistance is indicative of a condition that the soaking or wetness conditions of the liquid retention material are suitable for operation.

The threshold operation resistance may be set at 5 M$\Omega$, 4 M$\Omega$, 3 M$\Omega$, 2 M$\Omega$ or below.

The generator may be arranged such that an electrical resistance between said sensor and said electric heater that is above a threshold non-operation resistance is indicative of a condition that the soaking or wetness conditions of the liquid retention material is not suitable for operation.

The threshold non-operation resistance may be at 10 M$\Omega$, 20 M$\Omega$, 30 M$\Omega$, or above.

The flavoured vapour generator may be in the form of a cartridge, wherein power supply terminals for supply power to the electric heater and sensor terminals for obtaining soaking condition information are accessible from outside of the housing.

The flavoured vapour generator may be a cartomiser.

An electronic cigarette comprising a control device and a flavoured vapour generator is disclosed. The control device is to operate the electric heater upon determination of whether said flavoured vapour generator is at a wetness condition or a soaking condition that is suitable for normal operation.

The control device may be arranged not to operate said electric heater to heat the flavoured vapour generator to generate flavoured smoke upon determination that the soaking or wetness condition of said flavoured vapour generator corresponds to a condition of exhaustion or near exhaustion of said flavoured liquid in said liquid retention material.

The control device may be arranged not to operate said electric heater to heat the flavoured vapour generator to generate flavoured smoke upon determination that the resistance between said sensor and said electric heater is above a threshold non-operation resistance.

An electronic smoking apparatus comprising a flavoured vapour generating apparatus according to any of the preceding claims and an electronic controller, wherein the electronic controller is to control operation of the converter to generate smoke flavoured vapour with reference to output of the sensor.

While an electric heater is provided as an example of converter for converting flavoured liquid into flavoured vapour, the converter may not be limited to a heater and can be other atomising device such as ultra-sonic atomiser without loss of generality.

While examples have been provided herein to illustrate principles and embodiments of the disclosure, it should be appreciated that the examples are for reference only and shall not be construed as limiting the scope of disclosure. For example, while the cartomiser disclosed herein is in the form of a disposable cartridge, it should be appreciated that the cartomiser may be integrally formed with the electronic cigarette without loss of generality. For example, while the present disclosure has been described with reference to an example flavoured liquid known as e-juice or e-liquid, which is usually a solution comprising organic substances, such as propylene glycol (PG), vegetable glycerine (VG), polyethylene glycol 400 (PEG400) mixed with concentrated flavours, liquid nicotine concentrate, or a mixture thereof; it should be appreciated that the example used are merely example and other types of liquid suitable for electronic cigarette operation known from time to time may be used.

TABLE OF REFERENCE NUMERALS

| 100 | Vapour generator | | |
|---|---|---|---|
| 110 | Air inlet end | | |
| 120 | Air outlet end | | |
| 130 | Main body | 132 | Outer peripheral wall |
| | | 134 | Inner peripheral wall |
| | | 136 | reservoir |
| | | 138 | Passage channel |
| 140 | Base portion | | |
| 150 | converter | | |
| | | 152 | Heater wire |
| | | 154 | Naked liquid retention device |
| | | 155 | wicks |
| | | 156 | sensor |
| | | 157 | conductor |
| | | 158 | Wire frame |

The invention claimed is:

1. An electronic smoking apparatus comprising:
    a liquid reservoir configured to store a liquid;
    an electric heater configured to heat the liquid of the liquid reservoir to generate a vapor;
    a wick configured to draw liquid from the liquid reservoir, wherein a sensor is wound around the wick; and
    an electronic controller connected to ends of the sensor through respective first terminals, the electronic controller configured to
        measure an electrical resistance using the sensor, and
        detect depletion of the liquid in the liquid reservoir based on the electrical resistance of the sensor.

2. The electronic smoking apparatus according to claim 1, wherein the electronic controller is connected to ends of the electric heater through respective second terminals.

3. The electronic smoking apparatus according to claim 1, wherein the electric heater and the sensor are within the liquid reservoir.

4. The electronic smoking apparatus according to claim 1, wherein the liquid reservoir comprises:
    a reservoir housing defining an axially extending hollow passage channel, the reservoir housing having a first liquid outlet and a second liquid outlet, wherein
        the first liquid outlet and the second liquid outlet are in liquid communication with the axially extending hollow passage channel to supply liquid to the wick, and
        the wick extends between the first liquid outlet and the second liquid outlet.

5. The electronic smoking apparatus according to claim 1, wherein the electric heater includes a heating coil wound around the wick, the heating coil configured to heat the liquid on the wick to generate the vapor.

6. The electronic smoking apparatus according to claim 1, wherein
    the liquid includes one or more of propylene glycol (PG), vegetable glycerin (VG), polyethylene glycol 400 (PEG400), or other organic based solvents including glycol or glycerine based solvents.

7. The electronic smoking apparatus according to claim 1, wherein the electronic controller comprises:
    a resistance measurement circuit electrically contacting the ends of the sensor through the respective first terminals, the resistance measurement circuit configured to measure the electrical resistance of the sensor through the respective first terminals.

8. The electronic smoking apparatus according to claim 1, wherein the electronic controller further comprises:
    a control circuit configured to detect the depletion of the liquid in the liquid reservoir based on the electrical resistance of the sensor.

9. The electronic smoking apparatus according to claim 1, wherein
    the liquid reservoir, the sensor, and the electric heater are part of a cartomizer of the electronic smoking apparatus;
    the electronic controller is part of a main body of the electronic smoking apparatus; and
    the cartomizer is configured to be detachably coupled to the main body.

10. The electronic smoking apparatus according to claim 1, wherein the electronic controller is further configured to control power output to the electric heater to generate the vapor based on the depletion of the liquid in the liquid reservoir.

11. The electronic smoking apparatus according to claim 1, wherein the electronic controller is further configured to reduce power output to the electric heater in response to detecting depletion of the liquid in the liquid reservoir.

12. The electronic smoking apparatus according to claim 1, wherein the electronic controller is further configured to generate a warning signal in response to detecting depletion of the liquid in the liquid reservoir.

13. An electronic smoking apparatus comprising:
a liquid reservoir configured to store a liquid;
an electric heater configured to heat the liquid of the liquid reservoir to generate a vapor;
a wick configured to draw liquid from the liquid reservoir, wherein a sensor is wound around the wick; and
an electronic controller connected to ends of the sensor through respective first terminals, the electronic controller configured to
measure an electrical resistance using the sensor, and
determine whether the liquid in the liquid reservoir is at or above an operation threshold value based on the electrical resistance of the sensor.

14. The electronic smoking apparatus according to claim 13, wherein the electric heater and the sensor are within the liquid reservoir.

15. The electronic smoking apparatus according to claim 13, wherein the electronic controller is connected to ends of the electric heater through respective second terminals.

16. The electronic smoking apparatus according to claim 15, wherein the electronic controller is further configured to control power output to the electric heater through the respective second terminals to generate the vapor based on whether the liquid of the liquid reservoir is at or above the operation threshold value.

17. The electronic smoking apparatus according to claim 13, wherein the electronic controller is further configured to reduce power output to the electric heater and generate a warning signal in response to determining that the liquid of the liquid reservoir is below the operation threshold value.

18. The electronic smoking apparatus according to claim 13, wherein the liquid reservoir comprises:
a reservoir housing defining an axially extending hollow passage channel, the reservoir housing having a first liquid outlet and a second liquid outlet, wherein
the first liquid outlet and the second liquid outlet are in liquid communication with the axially extending hollow passage channel to supply liquid to the wick, and
the wick extends between the first liquid outlet and the second liquid outlet.

* * * * *